United States Patent [19]

Bietti et al.

[11] Patent Number: 4,649,150
[45] Date of Patent: Mar. 10, 1987

[54] ANTIULCEROGENIC AMIDINE DERIVATIVES OF 2-SUBSTITUTED 4-PHENYLIMIDAZOLE

[75] Inventors: Giuseppe Bietti, Milan; Enzo Cereda, Tortona; Arturo Donetti; Antonio Giachetti, both of Milan; Ferdinando Pagani, Verano Brianza, all of Italy

[73] Assignee: Istituto de Angeli, S.p.A., Milan, Italy

[21] Appl. No.: 610,958

[22] Filed: May 16, 1984

[30] Foreign Application Priority Data

Jul. 18, 1983 [IT] Italy ................................ 22110 A/83

[51] Int. Cl.⁴ .................. A61K 31/415; A61K 31/44; C07D 233/64; C07D 233/70
[52] U.S. Cl. .................... 514/392; 514/397; 514/398; 514/400; 514/401; 546/278; 548/315; 548/316; 548/318; 548/322; 548/336; 548/337; 548/346
[58] Field of Search ............. 548/346, 337, 315, 316, 548/322, 318, 336; 546/278; 514/397, 392, 398, 400, 341

[56] References Cited

U.S. PATENT DOCUMENTS 4,386,099 5/1983 Cereda et al. .................. 548/346 X Primary Examiner—Richard A. Schwartz
Attorney, Agent, or Firm—Hammond & Littell, Weissenberger & Dippert

[57] ABSTRACT

Compounds of the formula

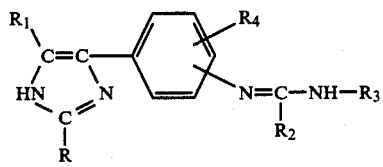

wherein
R represents substituents of various types;
$R_1$ and $R_2$ are each independently hydrogen or lower alkyl;
$R_3$ represents substituents of various types; and
$R_4$ is hydrogen, alkyl of 1 to 3 carbon atoms, alkoxy of 1 to 3 carbon atoms, halogen, cyano or carbamoyl;
tautomers thereof; and non-toxic, pharmacologically acceptable acid addition salts thereof. The compounds as well as their salts are useful as antiulcerogenics.

10 Claims, No Drawings

ANTIULCEROGENIC AMIDINE DERIVATIVES OF 2-SUBSTITUTED 4-PHENYLIMIDAZOLE

This invention relates to novel amidine derivatives of 2-substituted 4-phenylimidazole and non-toxic acid addition salts thereof, to methods of preparing these compounds, to pharmaceutical compositions containing them as active ingredients, and to methods of using them as gastric secretion inhibitors and antiulcerogenics.

More particularly, the present invention relates to a novel class of compounds represented by the formula

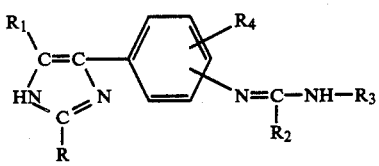

wherein
R is straight or branched lower alkyl, hydroxyl, alkoxy of 1 to 3 carbon atoms, mercapto, (alkyl of 1 to 3 carbon atoms)thio, halogen, (alkyl of 1 to 3 carbon atoms)sulfinyl, (alkyl of 1 to 3 carbon atoms)sulfonyl, sulfamoyl, amino, (alkyl of 1 to 3 carbon atoms)amino, di(alkyl of 1 to 3 carbon atoms)amino, lower alkanoylamino or phenyl;
$R_1$ and $R_2$ are each independently hydrogen or lower alkyl;
$R_3$ is straight or branched lower alkyl optionally containing a heteroatom such as oxygen, sulfur or nitrogen; lower alkenyl, lower alkynyl, cyano, optionally substituted aryl or aralkyl, cycloalkyl, cycloaliphatic alkyl, substituted or unsubstituted heterocyclylalkyl, or substituted or unsubstituted heterocyclyl;
$R_4$ is hydrogen, alkyl of 1 to 3 carbon atoms, alkoxy of 1 to 3 carbon atoms, halogen, cyano or carbamoyl; tautomers thereof; and non-toxic, pharmacologically acceptable acid addition salts thereof.

The compounds embraced by formula I are basic and therefore form addition salts with inorganic or organic acids. Examples of non-toxic, pharmacologically acceptable acid addition salts are those formed with hydrochloric, hydrobromic, nitric, sulfuric, acetic, maleic, fumaric, citric or tartaric acid.

Suitable acids are hydrochloric acid, sulfuric acid, maleic acid and fumaric acid.

It should be understood that, for convenience, in this specification reference will be made indifferently either to the compounds as bases or to the corresponding salts.

It is to be pointed out that, although in formula (I) the double bond in the amidine radical and in the imidazolyl ring has been inserted in a particular position, various other tautomeric forms are possible. Furthermore, the compounds in which R is hydroxyl or mercapto may be in the corresponding imidazolinone or imidazolinthione forms. The present invention includes such tautomeric forms as regards both the compounds and the methods of preparation.

When R in formula (I) represents a linear or branched alkyl group, it may be an alkyl group having 1-4 carbon atoms; when $R_1$ and $R_2$ represent an alkyl group this may be alkyl group having 1-4 carbon atoms; when $R_3$ represents a linear or branched alkyl group it may be an alkyl group having 1-8 carbon atoms which may optionally contain an oxygen atom such as hydroxypropyl or methoxyethyl, a sulfur atom such as methylthioethyl or ethylthioethyl, or a nitrogen atom such as cyanoethyl; when $R_3$ is an alkenyl group, it may be an alkenyl group having 3-5 carbon atoms; when $R_3$ is an alkynyl group it may be an alkynyl group having 3 or 4 carbon atoms; when $R_3$ is a cycloalkyl or cycloaliphatic alkyl group, the ring may contain from 3 to 6 carbon atoms; when $R_3$ is an aryl group, it may be an optionally substituted phenyl group; when $R_3$ is an aralkyl group, it may be a benzyl group whose aromatic moiety may be substituted; when $R_3$ is a heterocyclic or a heterocyclylalkyl group, it may be an unsaturated, optionally substituted five or six-membered ring having one or more heteroatoms.

In the above-mentioned formula (I) the amidine radical may be in the ortho-, meta- or para-position of the benzene ring with respect to the imidazolyl group, and $R_4$ may be in any position in the benzene ring.

The compounds of the formula (I) may, for example, be prepared by the following methods.

Method A:
Reaction of a compound of the formula

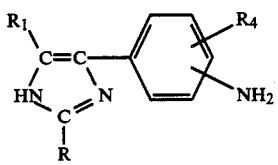

wherein R, $R_1$ and $R_4$ have the meanings previously defined, with a reactive derivative of a carboxamide of the formula

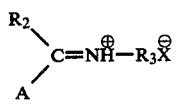

wherein $R_2$ and $R_3$ have the meanings previously defined, $X^\ominus$ represents the anion of an inorganic acid such as hydrochloride or fluoroborate, and A represents a benzoyloxy group, chlorine or a lower alkoxy group such as methoxy or ethoxy. If desired, the compound of the formula III may also be reacted as a base. The reaction is generally effected at a temperature from 0° to 100° C., preferably from 20° to 60° C. The reaction is advantageously carried out in the presence of an insert organic solvent. Suitable solvents include, for example, alkanols of 1 to 3 carbon atoms such as methanol or ethanol, and halogenated hydrocarbons such as dichloroethane, dioxane or acetone.

The starting compounds of the formula III may be obtained by conventional methods, for instance by reacting a carboxamide of the formula

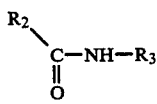

wherein $R_2$ and $R_3$ have the meanings previously defined, with benzoylchloride, triethyloxomium fluoroborate, ethyl chloroformate, phosphorus oxychloride or phosphorus pentachloride.

Method B:

Reaction of an N,N'-disubstituted amidine compound of the formula

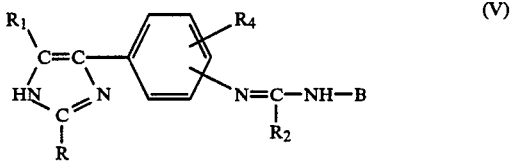

wherein R, R₁, R₂ and R₄ have the meanings previously defined, and B represents a suitable leaving group, such as cyano, acetyl, carbethoxy or carbamyl, with an amine of the formula $$H_2N-R_3 \quad (VI)$$

wherein R₃ has the meanings previously defined.

The reaction is advantageously performed in the presence of water or of an inert organic solvent, for example an alkanol, such as methanol or ethanol, formamide, dioxane or acetonitrile. This reaction may be effected at a temperature from 10°–50° C., preferably at room temperature. The starting compounds of the formula (V) may be prepared by methods described in the literature, for example, by reacting a compound of the formula II with an N-substituted ethyl imidate of the formula

wherein R₂ and B have the meanings previously defined, or optionally, when B in formula (V) represents a cyano group, the reaction may also be carried out in a single step by reacting a compound of the formula II with cyanamide in the presence of a compound of the formula

in which R₂ has the meanings previously defined and Y is lower alkyl, such as methyl or ethyl.

The reaction is generally carried out in the presence of a suitable inert organic solvent, for example a lower alkanol, an ether, ethylacetate, acetonitrile or dioxane, or without a solvent at a temperature from 20° to 80° C. The compound of the formula (VII) may be prepared by conventional methods.

The following examples illustrate the present invention and will enable others skilled in the art to understand it more completely. It should be understood, however, that the invention is not limited solely to the particular examples given below.

Preparation of starting compounds:

EXAMPLE 1

2-Methyl-4-(4-nitro-phenyl)-1H-imidazole

A mixture of 4-nitro-phenacyl bromide (100 g), acetamide (300 g), and water (15 g) was stirred at 140° C. for 8 hours, and was then poured into water (1500 ml). The resulting solution was filtered and made alkaline with 10% sodium hydroxide. The solid which separated out was filtered off, washed with water and dried to give 48.1 g of the title compound. M.p. 216°–219° C.

Using the above procedure, and starting with the appropriate phenacyl bromide and the appropriate amide, the following nitrophenyl imidazole derivatives were also prepared:

| | | |
|---|---|---|
| (a) | 2-Methyl-4-(3-nitro-phenyl)-1H—imidazole | M.p. 146–147° C. |
| (b) | 2-Ethyl-4-(4-nitro-phenyl)-1H—imidazole | M.p. 204–205° C. |
| (c) | 2-Isopropyl-4-(4-nitro-phenyl)-1H—imidazole | M.p. 201–205° C. |
| (d) | 2,5-Dimethyl-4-(4-nitro-phenyl)-1H—imidazole | M.p. 234–235° C. |
| (e) | 2-Methyl-4-(3-bromo-4-acetamido-phenyl)-1H—imidazole | M.p. 152–154° C. |
| (f) | 2-Phenyl-4-(4-nitro-phenyl)-1H—imidazole | M.p. 231–233° C. |

EXAMPLE 2

2-Methyl-4-(4-amino-phenyl)-1H-imidazole

A solution of 2-methyl-4-(4-nitro-phenyl)-1H-imidazole (28 g) in methanol (210 ml) was hydrogenated in the presence of 10% palladium-on-charcoal (1.35 g) at atmospheric pressure and at room temperature. After the calculated amount of hydrogen had been taken up, the catalyst was filtered off and the solution was evaporated to dryness to give 23.2 g of the title compound as a spongy solid. Using the above procedure, and starting from the appropriate nitrophenyl derivative, the following aminophenyl derivatives were also prepared:

| | | |
|---|---|---|
| (a) | 2-Methyl-4-(3-amino-phenyl)-1H—imidazole | M.p. 135–136° C. |
| (b) | 2-Ethyl-4-(4-amino-phenyl)-1H—imidazole | M.p. spongy solid |
| (c) | 2-Isopropyl-4-(4-amino-phenyl)-1H—imidazole | M.p. spongy solid |
| (d) | 2,5-Dimethyl-4-(4-amino-phenyl)-1H—imidazole | M.p. 190–192° C. |
| (e) | 2-Methoxy-4-(4-amino-phenyl)-1H—imidazole | M.p. 242–244° C. |
| (f) | 2-Acetamido-4-(4-amino-phenyl)-1H—imidazole | M.p. 215–216° C. |
| (g) | 2-Amino-4-(4-amino-phenyl)-1H—imidazole | M.p. 143–144° C. |
| (h) | 2-Methyl-4-(3-methyl-4-amino-phenyl)-1H—imidazole | M.p. 135–136° C. |
| (i) | 2-Methyl-4-(3-methoxy-4-amino-phenyl)-1H—imidazole | M.p. 167–168° C. |
| (j) | 2-Phenyl-4-(4-amino-phenyl)-1H—imidazole | M.p. 198–199° C. |

EXAMPLE 3

2-Methylthio-4-(4-nitro-phenyl)-1H-imidazole

2-Mercapto-4-(4-nitro-phenyl)-1H-imidazole (21.1 g) was added in portions to a solution of sodium (2.3 g) in ethanol (190 ml). After 15 minutes of stirring, a solution of iodomethane (14.2 g) in ethanol (50 ml) was added dropwise. After an additional 2 hours of stirring at room temperature, the solution was evaporated to dryness. The residual solid was treated with water, filtered off and dried to give 18.1 g of the title compound.

M.p. 200°–202° C.

(a) 2-Methoxy-4-(4-nitro-phenyl)-1H-imidazole (M.p. 295°–300° C.) was also prepared by this procedure, starting from 2-hydroxy-4-(4-nitro-phenyl)-1H-imidazole.

EXAMPLE 4

2-Methylthio-4-(4-amino-phenyl)-1H-imidazole

Concentrated hydrochloric acid (60 ml) was added dropwise to a stirred suspension of 2-methylthio-4-(4-nitro-phenyl)-1H-imidazole (5.88 g) and granulated tin (8.9 g) in water (25 ml). After an additional 3 hours of stirring at 100° C., the mixture was cooled to room temperature and filtered. The filter cake was dissolved in water, and the solution was filtered and evaporated to dryness. The residual solid was washed with ethanol, filtered off and treated with an ethanolic solution of sodium ethoxyde to give the free base (3 g).
M.p. 85°–86° C.

Using the above procedure, the appropriate nitrophenyl derivatives were reduced to give the following amines:

| | |
|---|---|
| (a) 2-Chloro-4-(4-amino-phenyl)-1H—imidazole | M.p. 56–58° C. |
| (b) 2-Methylsulfinyl-4-(4-amino-phenyl)-1H—imidazole | M.p. 83–85° C. |
| (c) 2-Sulfamoyl-4-(4-amino-phenyl)-1H—imidazole | M.p. 111–113° C. |

EXAMPLE 5

2-Chloro-4-(4-nitro-phenyl)-1H-imidazole

A mixture to 2-hydroxy-4-(4-nitro-phenyl)-1H-imidazole (15 g) and phosphorous oxychloride (750 ml) was refluxed, while stirring, for 24 hours. The solution was then evaporated to dryness, the residue was adjusted to pH 6.5 with a $H_2PO_4^-/HPO_4^{--}$ buffer, and extracted with methylene chloride. After drying, the organic solution was evaporated, and the crude product was chromatographed on silica gel to give 6.7 g of the title compound. M.p. 136°–138° C.

EXAMPLE 6

2-Methylsulfinyl-4-(4-nitrophenyl)-1H-imidazole

Hydrogen peroxide (36%, 100 ml) was added over a period of 2 hours, while stirring, to a hot (60° C.) solution of 2-methylthio-4-(4-nitro-phenyl)-1H-imidazole (19.6 g) in methanol (500 ml). After an additional 24 hours of heating at 60° C., the mixture was cooled to room temperature, filtered, and the filter cake was dried to give 16.1 g of the title compound.
M.p. 220°–222° C.

EXAMPLE 7

2-Sulfamoyl-4-(4-nitro-phenyl)-1H-imidazole

Chlorine was introduced through a capillary tube at a moderately rapid rate for 40 minutes into a stirred ice-cooled mixture of 2-mercapto-4-(4-nitro-phenyl)-1H-imidazole (10 g) in 1N hydrochloric acid (100 ml). The sulfonyl chloride which separated out was filtered, washed with cold water and added to an excess of liquid ammonia. After evaporation of the excess ammonia, the residue was taken up in a little dilute ammonium hydroxide and filtered with charcoal. The filtrate was cooled and made slightly acidic, the solid which separated out was filtered off and recrystallized from water to give 3.4 g of the title compound. M.p. 227°–229° C.

EXAMPLE 8

2-Amino-4-(4-nitro-phenyl)-1H-imidazole

A mixture of α-amino-4-nitro-acetophenone hydrochloride (70 g), cyanamide (40.7 g), water (2100 ml) and concentrated acetic acid (70 ml) was adjusted to pH 4.5 with 30% sodium hydroxide and heated at 100° C. for 45 minutes. The hot solution was filtered and cooled. The solid which separated out was filtered off, washed with water and dried to give 25 g of the title compound.
M.p. 235°–240° C. (as hydrochloride).

EXAMPLE 9

2-Acetamido-4-(4-nitro-phenyl)-1H-imidazole

A mixture of 2-amino-4-(4-nitro-phenyl)-1H-imidazole (17.3 g) and acetic anhydride (100 ml) was heated at 100° C. for one hour. The resulting solution was evaporated to dryness, and the residue was treated with ether, filtered off and dried to give 18.9 g of the title compound.
M.p. 242°–244° C.

EXAMPLE 10

2-Ethylamino-4-(4-amino-phenyl)-1H-imidazole

A suspension of 2-acetamido-4-(4-amino-phenyl)-1H-imidazole (16 g) in anhydrous tetrahydrofuran (160 ml) was added dropwise to a stirred suspension of lithium aluminum hydride (12 g) in anhydrous tetrahydrofuran (240 ml). The mixture was heated at 60° C. for 4 hours.
After cooling and treatment with water, the solvent was evaporated, and the residue was dissolved in 10% hydrochloric acid. The solution was made alkaline with 30% sodium hydroxide, and the base was extracted with ethyl acetate. The organic phase was evaporated to dryness to give 8.2 g of the title compound.
M.p. 89°–91° C.

EXAMPLE 11

2-Methyl-4-(3-bromo-4-amino-phenyl)-1H-imidazole

A mixture of 2-methyl-4-(3-bromo-4-acetamido-phenyl)-1H-imidazole (15 g), concentrated hydrochloric acid (10 ml) and water (30 ml) was refluxed for 45 minutes. The resulting solution was cooled to room temperature and was made alkaline with 10% sodium hydroxide. The base was filtered off, washed with water and dried to give 10 g of the title compound.
M.p. 34°–36° C.

EXAMPLE 12

2-Methyl-4-(3-cyano-4-amino-phenyl)-1H-imidazole

A mixture of 2-methyl-4-(3-bromo-4-amino-phenyl)-1-imidazole (5.12 g), copper (I) cyanide (2 g) and quinoline (15 ml) was refluxed for 4 hours. After cooling and decomposition with an acid solution of ferric chloride, the mixture was extracted with ethyl acetate. The organic solution was dried and evaporated to dryness, and the residue was treated with water, filtered off and dried to give 2.1 g of the title compound.
M.p. 89°–91° C.

EXAMPLE 13

2-Methyl-4-(3-carbamoyl-4-amino-phenyl)-1H-imidazole

A mixture of 2-methyl-4-(3-cyano-4-amino-phenyl)-1H-imidazole (6.2 g), the ion exchanger Amerlite ®

IRA 400 (OH) (12 g) and water (150 ml) was refluxed for 5 hours. After cooling and filtration, the resulting solution was evaporated to dryness to give 4.1 g of the title compound.

M.p. 137°–139° C.

EXAMPLE 14

2-Methyl-4-(3-methyl-4-nitro-phenyl)-1H-imidazole

2-Methyl-4-(3-methyl-phenyl)-1H-imidazole nitrate (15 g) was added portionwise to 96% sulfuric acid (40 ml) at room temperature. The resulting solution was heated at 90° C. for one hour, cooled, diluted with water (200 ml) and neutralized with aqueous sodium carbonate. The solid which separated out was filtered off, and the filtrate was made strongly alkaline with 10% sodium hydroxide. The base which precipitated was filtered off and dried to give 5 g of the title compound sufficiently pure to be used in the next step.

M.p. 158°–160° C.

The following starting compound was prepared in analogous manner: 2-Methyl-4-(3-methoxy-4-nitrophenyl)-1H-imidazole, M.p. 191°–192° C.

Preparation of end products of the formula I:

EXAMPLE 15

N-Cyano-N'-[4-(2-methyl-imidazol-4-yl)phenyl]-formamidine

A solution of 2-methyl-4-(4-amino-phenyl)-1H-imidazole (15 g) and ethyl N-cyanoformimidate (9.35 g) in ethanol (150 ml) was stirred at room temperature overnight. The product which crystallized out was collected by filtration, washed with cold ethanol and dried to give 15.2 g of the title compound.

M.p. 175°–176° (dec.).

Using the above procedure, and starting with the appropriate starting compound, the following N-cyanoamidines were also prepared:

(a) N-cyano-N'-[3-(2-methyl-imidazol-4-yl)phenyl]-formamidine, M.p. 225°–230° C. (dec.)
(b) N-cyano-N'-[4-(2-ethyl-imidazol-4-yl)phenyl]-formamidine, M.p. 227°–229° C. (dec.)
(c) N-cyano-N'-[4-(2-isopropyl-imidazol-4-yl)phenyl]-formamidine M.p. 221°–223° C. (dec.)
(d) N-cyano-N'-[4-(2-methyl-imidazol-4-yl)phenyl]-acetamidine M.p. 152°–153° C. (dec.)
(e) N-cyano-N'-[4-(2,5-dimethyl-imidazol-4-yl)phenyl]-formamidine, M.p. 145°–148° C. (dec.)
(f) N-Cyano-N'-[4-(2-mercapto-imidazol-4-yl)phenyl]-formamidine, M.p. 270° C. (dec.)
(g) N-Cyano-N'-[4-(2-methylmercapto-imidazol-4-yl)phenyl]-formamidine, M.p. 232°–235° C. (dec.)
(h) N-Cyano-N'-[4-(2-hydroxy-imidazol-4-yl)phenyl]-formamidine, M.p. 255°–258° C. (dec.)
(i) N-Cyano-N'-[4-(2-methoxy-imidazol-4-yl)phenyl]-formamidine, M.p. 270° C. (dec.)
(j) N-Cyano-N'-[4-(2-sulfamoyl-imidazol-4-yl)phenyl]-formamidine, M.p. 241°–242° C. (dec.)
(k) N-Cyano-N'-[4-(2-acetamido-imidazol-4-yl)phenyl]-formamidine, M.p. 228°–230° C. (dec.)
(l) N-Cyano-N'-[4-(2-ethyl-amino-imidazol-4-yl)phenyl]-formamidine, M.p. 215°–216° C. (dec.)
(m) N-Cyano-N'-[2-bromo-4-(2-methyl-imidazol-4-yl)phenyl]-formamidine, M.p. 247°–248° C. (dec.)
(n) N-Cyano-N'-[2-cyano-4-(2-methyl-imidazol-4-yl)phenyl]-formamidine, M.p. 239°–241° C. (dec.)
(o) N-Cyano-N'-[2-carbamoyl-4-(2-methyl-imidazol-4-yl)phenyl]-formamidine, M.p. 250°–252° C. (dec.)
(p) N-Cyano-N'-[4-(2-amino-imidazol-4-yl)phenyl]-formamidine, M.p. 220°–222° C. (dec.)
(q) N-Cyano-N'-[2-methyl-4-(2-methyl-imidazol-4-yl)phenyl]-formamidine, M.p. 234°–236° C. (dec.)
(r) N-Cyano-N'-[2-methoxy-4-(2-methyl-imidazol-4-yl)phenyl]-formamidine, M.p. 263°–266° C. (dec.)
(s) N-Cyano-N'-[4-(2-phenyl-imidazol-4-yl)phenyl]-formamidine, M.p. >280° C.
(t) N-Cyano-N'-[4-(2-methyl-sulfinyl-imidazol-4-yl)phenyl]-formamidine, M.p. 222°–224° C. (dec.).

EXAMPLE 16

N-Methyl-N'-[4-(2-methyl-imidazol-4-yl)phenyl]-formamidine

N-Cyano-N'-[4-(2-methyl-imidazol-4-yl)phenyl]-formamidine (2.25 g) was added all at once to a solution of methylamine 33% aqueous (22.5 ml). After a few minutes the solid which separated out was filtered off, washed with water and dried to give 1.2 g of the title compound.

Maleate salt (ethanol) M.p. 173°–174° C. (dec.)

Analysis: $C_{20}H_{22}N_4O_8$ Found %: C-54.07; H-4.79; N-12.31. Calc. %: C-53.81; H-4.97; N-12.55.

The following compounds were prepared in analogous manner, starting from the appropriate N-cyanoamidine derivative previously described:

(a) N-Ethyl-N'-[4-(2-methyl-imidazol-4-yl)phenyl]-formamidine.
Maleate salt (ethanol) M.p. 166°–168° C. (dec.)
Analysis: $C_{21}H_{24}H_4O_8$ Found %: C-54.49; H-5.21; N-12.38. Calc. %: C-54.78; H-5.25; N-12.17.

(b) N-Isopropyl-N'-[4-(2-methyl-imidazol-4-yl)phenyl]-formamidine. Maleate salt (ethanol) M.p. 192°–193° C. (dec.)
Analysis: $C_{22}H_{26}N_4O_8$ Found %: C-55.84; H-5.59; N-11.63. Calc. %: C-55.69; H-5.52; N-11.81.

(c) N-Allyl-N'-[4-(2-methyl-imidazol-4-yl)phenyl]-formamidine. Maleate salt (ethanol), M.p. 170°–171° C. (dec.)
Analysis: $C_{22}H_{24}N_4O_8$ Found %: C-56.17; H-5.00; N-12.08. Calc. %: C-55.93; H-5.12; N-11.86.

(d) N-Propargyl-N'-[4-(2-methyl-imidazol-4-yl)phenyl]-formamidine. Maleate salt (ethanol). M.p. 160°–162° C. (dec.)
Analysis: $C_{22}H_{22}N_4O_8$ Found %: C-56.23; H-4.70; N-12.05. Calc. %: C-56.17; H-4.71; N-11.91.

(e) N-n-Hexyl-N'-[4-(2-methyl-imidazol-4-yl)phenyl]-formamidine. Maleate salt (acetone). M.p. 127°–130° C. (dec.)
Analysis: $C_{25}H_{32}N_4O_8$ Found %: C-57.87; H-6.24; N-10.62. Calc. %: C-58.13; H-6.24; N-10.85.

(f) N-(2-Methoxyethyl)-N'-[4-(2-methyl-imidazol-4-yl)phenyl]-formamidine. Maleate salt (acetone). M.p. 161°–163° C. (dec.)
Analysis: $C_{22}H_{26}N_4O_9$ Found %: C-54.13; H-5.29; N-11.28. Calc. %: C-53.87; H-5.34; N-11.42.

(g) N-(3-Hydroxypropyl)-N'-[4-(2-methyl-imidazol-4-yl)phenyl-formamidine. Maleate salt (acetone). M.p. 166°–169° C. (dec.).
Analysis: $C_{22}H_{26}N_4O_9$ Found %: C-53.57; H-5.21; N-11.59. Calc. %: C-53.87; H-5.34; N-11.42.

(h) N-(2-Methylthioethyl)-N'-[4-(2-methyl-imidazol-4-yl)phenyl]-formmidine. Maleate salt (ethanol). M.p. 170°–172° C. (dec.)
Analysis: $C_{22}H_{26}N_4O_8S$ Found %: C-51.99; H-5.27; N-11.30. Calc. %: C-52.17; H-5.18; N-11.06.

(i) N-(2-(Cyanoethyl)-N'-[4-(2-methyl-imidazol-4-yl)phenyl]formamidine. Maleate salt (ethanol). M.p. 162°–164° C. (dec.).
Analysis: $C_{22}H_{23}N_5O_8$ Found %: C-54.29; H-4.71; N-14.35. Calc. %: C-54.43; H-4.78; N-14.43.

(j) N-Cyclopropylmethyl-N'-[4-(2-methyl-imidazol-4-yl)-phenyl]-formamidine. Fumarate salt (ethanol). M.p. 154°–157° C. (dec.)
Analysis: $C_{23}H_{26}N_4O_8$ Found %: C-56.60; H-5.30; N-11.53. Calc. %: C-56.78; H-5.39; N-11.52.

(k) N-Cyclohexyl-N'-[4-(2-methyl-imidazol-4-yl)phenyl]-formamidine. Fumarate salt (ethanol). M.p. 164°–166° C. (dec.)
Analysis: $C_{25}H_{30}N_4O_8$ Found %: C-58.07; H-5.95; N-11.00. Calc. %: C-58.36; H-5.88; N-10.89.

(l) N-Benzyl-N'-[4-(2-methyl-imidazol-4-yl)phenyl]-formmidine. Hydrochloride salt (ethanol). M.p. 225°–227° C. (dec.)
Analysis $C_{18}H_{20}Cl_2N_4$ Found %: C-59.39; H-5.65; N-15.63. Calc. %: C-59.51; H-5.55; N-15.42.

(m) N-Furfuryl-N'-[4-(2-methyl-imidazol-4-yl)phenyl]-formamidine. Hydrochloride salt (ethanol). M.p. 235°–237° C. (dec.)
Analysis: $C_{16}H_{18}Cl_2N_4O$ Found %: C-54.67; H-5.27; N-15.68. Calc. %: C-54.40; H-5.14; N-15.86.

(n) N-Ethyl-N'-[4-(2-ethyl-imidazol-4-yl)-phenyl]-formamidine Maleate salt (ethanol). M.p. 165°–167° C. (dec.)
Analysis: $C_{22}H_{26}N_4O_8$ Found %: C-55.78; H-5.51; N-11.59. Calc. %: C-55.69; H-5.52; N-11.81.

(o) N-Isopropyl-N'-[4-(2-ethyl-imidazol-4-yl)phenyl]-formamidine. Maleate salt (ethanol). M.p. 180°–181° C. (dec.)
Analysis: $C_{23}H_{28}N_4O_8$ Found %: C-56.95; H-5.79; N-11.30. Calc. %: C-56.55; H-5.78; N-11.47.

(p) N-Ethyl-N'-[4-(2-isopropyl-imidazol-4-yl)phenyl]-formamidine. Maleate salt (ethanol). M.p. 174°–175° C. (dec.)
Analysis: $C_{23}H_{28}N_4O_8$ Found %: C-56.73; H-5.87; N-11.60. Calc. %: C-56.55; H-5.78; N-11.47.

(q) N-Isopropyl-N'-[4-(2-isopropyl-imidazol-4-yl)phenyl]-formamidine. Maleate salt (ethanol). M.p. 168°–170° C. (dec.)
Analysis: $C_{24}H_{30}N_4O_8$ Found %: C-57.02; H-6.10; N-11.28. Calc. %: C-57.36; H-6.02; N-11.15.

(r) N-Isopropyl-N'-[4-(2-phenyl-imidazol-4-yl)phenyl]-formamidine. Maleate salt (ethanol). M.p. 208°–210° C. (dec.)
Analysis: $C_{23}H_{24}N_4O_4$ Found %: C-66.01; H-5.95; N-13.20. Calc. %: C-65.70; H-5.75; N-13.33.

(s) N-Isopropyl-N'-[4-(2-methyl-imidazol-4-yl)phenyl]-acetamidine. Maleate salt (ethanol). M.p. 106°–108° C. (dec.)
Analysis: $C_{23}H_{28}N_4O_8$ Found %: C-56.67; H-5.76; N-11.55. Calc %: C-56.55; H-5.78; N-11.47.

(t) N-Ethyl-N'-[4-(2,5-dimethyl-imidazol-4-yl)phenyl]-formamidine. Maleate salt (acetone). M.p. 165°–167° C. (dec.)
Analysis: $C_{22}H_{26}N_4O_8$ Found %: C-55.41; H-5.70; N-12.01. Calc. %: C-55.69; H-5.52; N-11.81.

(u) N-Isopropyl-N'-[4-(2,5-dimethyl-imidazol-4-yl)phenyl]-formamidine. Maleate salt (acetone). M.p. 157°–159° C. (dec.)
Analysis: $C_{23}H_{28}N_4O_8$ Found %: C-56.38; H-5.82; N-11.59. Calc. %: C-56.55; H-5.78; N-11.47.

(v) N-Ethyl-N'-[3-(2-methyl-imidazol-4-yl)phenyl]-formamidine. Maleate salt (acetone). M.p. 171°–173° C. (dec.)
Analysis: $C_{21}H_{24}N_4O_8$ Found %: C-54.61; H-5.19; N-11.98. Calc. %: C-54.78; H-5.25; N-12.17.

(w) N-Isopropyl-N'-[3-(2-methyl-imidazol-4-yl)phenyl]-formamidine. Maleate salt (acetone). M.p. 168°–171° C. (dec.)
Analysis: $C_{22}H_{26}N_4O_8$ Found %: C-55.44; H-5.48; N-11.69. Calc. %: C-55.69; H-5.52; N-11.81.

(x) N-Isopropyl-N'-[4-(2-mercapto-imidazol-4-yl)phenyl]-formamidine. Maleate salt (acetone). M.p. 202° C. (dec.)
Analysis: $C_{17}H_{20}N_4O_4S$ Found %: C-54.38; H-5.33; N-14.70. Calc. %: C-54.24; H-5.35; N-14.88.

(y) N-Ethyl-N'-[4-(2-methylmercapto-imidazol-4-yl)phenyl]-formamidine. Maleate salt (ethanol). M.p. 158°–160° C. (dec.)
Analysis: $C_{21}H_{24}N_4O_8S$ Found %: C-51.31; H-5.00; N-11.28. Calc. %: C-51.22; H-4.91; N-11.39.

(z) N-Isopropyl-N'-[4-(2-methylmercapto-imidazol-4-yl)phenyl]-formamidine. Maleate salt (acetone). M.p. 150°–152° C. (dec.)
Analysis: $C_{22}H_{26}N_4O_8S$ Found %: C-51.93; H-5.20; N-11.25. Calc. %: C-52.17; H-5.18; N-11.06.

(aa) N-Isopropyl-N'-[4-(2-hydroxy-imidazol-4-yl)phenyl]-formamidine. Maleate salt (acetone). M.p. 211°–213° C. (dec.)
Analysis: $C_{17}H_{20}N_4O_5$ Found %: C-56.47; H-5.69; N-15.58. Calc. %: C-56.66; H-5.59; N-15.55.

(ab) N-Isopropyl-N'-[4-(2-methylsulfinyl-imidazol-4-yl)phenyl]-formamidine. Base (water). M.p. 200°–201° C. (dec.)
Analysis: $C_{14}H_{18}N_4OS$ Found %: C-57.82; H-6.23; N-19.15. Calc. %: C-57.92; H-6.25; N-19.30.

(ac) N-Isopropyl-N'-[4-(2-sulfamoyl-imidazol-4-yl)phenyl]-formamidine. Maleate salt (acetone). M.p. 243°–246° C. (dec.)
Analysis: $C_{17}H_{21}N_5O_6S$ Found %: C-47.97; H-5.07; N-16.63. Calc. %: C-48.22; H-5.00; N-16.54.

(ad) N-Isopropyl-N'-[4-(2-amino-imidazol-4-yl)phenyl]-formamidine. Maleate salt (ethanol). M.p. 212°–215° C. (dec.)
Analysis: $C_{21}H_{25}N_5O_8$ Found %: C-52.80; H-5.23; N-14.81. Calc. %: C-53.05; H-5.30; N-14.73.

(ae) N-Isopropyl-N'-[4-(2-acetamido-imidazol-4-yl)phenyl]-formamidine. Maleate salt (acetone). M.p. 196°–198° C. (dec.)
Analysis: $C_{23}H_{27}N_5O_9$ Found %: C-53.40; H-5.22; N-13.44. Calc. %: C-53.38; H-5.26; N-13.53.

(af) N-Isopropyl-N'-[4-(2-ethylamino-imidazol-4-yl)phenyl]-formamidine. Maleate salt (ethanol). M.p. 225°–227° C. (dec.)
Analysis: $C_{23}H_{29}N_5O_8$ Found %: C-54.50; H-5.73; N-14.09. Calc. %: C-54.86; H-5.81; N-13.91.

(ag) N-n-Propyl-N'-[2-bromo-4-(2-methyl-imidazol-4-yl)phenyl]-formamidine. Maleate salt (acetone). M.p. 186°–188° C. (dec.)
Analysis: $C_{22}H_{25}BrN_4O_8$ Found %: C-47.66; H-4.60; N-10.01. Calc. %: C-47.75; H-4.55; N-10.12.

(ah) N-Isopropyl-N'-[2-cyano-4-(2-methyl-imidazol-4-yl)phenyl]-formamidine. Maleate salt (ethanol). M.p. 178°–180° C. (dec.)
Analysis: $C_{23}H_{25}N_5O_8$ Found %: C-55.12; H-4.99; N-13.88. Calc. %: C-55.30; H-5.05; N-14.02.

(ai) N-Ethyl-N'-[2-carbamoyl-4-(2-methyl-imidazol-4-yl)phenyl]-formamidine. Maleate salt (acetone). M.p. 233°–235° C. (dec.)
Analysis: $C_{22}H_{25}N_5O_9$ Found %: C-52.63; H-5.09; N-14.10; Calc. %: C-52.48; H-5.01; N-13.91.

(aj) N-Allyl-N'-[2-methyl-4-(2-methyl-imidazol-4-yl)phenyl]-formamidine. Maleate salt (acetone). M.p. 170°-172° C. (dec.)

Analysis: $C_{23}H_{26}N_4O_8$ Found %: C-57.00; H-5.45; N-11.38. Calc. %: C-56.78; H-B 5.39; N-11.52.

(ak) N-n-Propyl-N'-[2-methoxy-4-(2-methyl-imidazol-4-yl)phenyl]-formamidine. Maleate salt (acetone). M.p. 201°-203° C. (dec.)

Analysis: $C_{22}H_{28}N_4O_9$ Found %: C-54.44; H-5.59; N-10.97. Calc. %: C-54.75; H-5.59; N-11.11.

EXAMPLE 17

N-tert.Butyl-N'-[4-(2-methyl-imidazol-4-yl)phenyl]-formamidine

A solution of triethyloxonium fluoroborate (9.56 g) in dichloromethane (50 ml) was slowly added to a solution of N-tert.butyl-formamide (5.06 g) in dichloromethane (30 ml). After six hours of stirring at room temperature, 2-methyl-4-(4-aminophenyl)-1H-imidazole (4 g) in ethanol (20 ml) was added dropwise.

The mixture was stirred overnight, and was then evaporated to dryness. The fluoroborate salt of the desired compound thus obtained was dissolved in water, and the solution was made alkaline with 10% sodium hydroxide. The product which separated out was filtered off, washed with water and dried to give 2.1 g of the title compound.

Sulfate salt (methanol). M.p. 276°-278° C. (dec.).

Analysis: $C_{15}H_{22}N_4O_4S$ Found %: C-50.79; H-6.31; N-15.77. Calc. %: C-50.84; H-6.26; N-15.81.

EXAMPLE 18

N-Phenyl-N'-[4-(2-methyl-imidazol-4-yl)phenyl]-formamidine

2-Methyl-4-(4-amino-phenyl)-1H-imidazole (5 g) was added to a solution of ethyl N-phenyl-formamidate (5 g) in acetone (25 ml). After 3 hours of stirring at room temperature, the solid which separated out was filtered off and dried. The product was treated with glacial acetic acid in acetone. The acetate salt which precipitated was filtered off and dried to give 4.6 g of the title compound.

Acetate salt (acetone). M.p. 147°-150° C. (dec.).

Analysis: $C_{21}H_{24}N_4O_4$ Found %: C-63.77; H-6.13; N-14.27. Calc. %: C-63.62; H-6.10; N-14.13.

The following compounds were prepared in analogous manner, starting from the appropriate ethyl formimidate:

(a) N-(4-Chlorophenyl)-N'-[4-(2-methyl-imidazol-4-yl)phenyl]-formamidine.

Acetate salt (acetone). M.p. 112°-115° C. (dec.).

Analysis: $C_{21}H_{23}ClN_4O_4$ Found %: C-58.29; H-5.60; N-13.12. Calc. %: C-58.54; H-5.38; N-13.00.

(b) N-(2-Pyridyl)-N'-[4-(2-methyl-imidazol-4-yl)phenyl]-formamidine

Base (acetone). M.p. 59°-61° C. (dec.).

Analysis: $C_{16}H_{15}N_5$ Found %: C-68.99; H-5.30; N-25.36. Calc. %: C-69.29; H-5.45; N-25.26.

(c) N-Isopropyl-N'-[4-(2-chloro-imidazol-4-yl)phenyl]-formamidine

Base (acetone). M.p. 85°-87° C. (dec.).

Analysis: $C_{12}H_{13}ClN_4$ Found %: C-57.89; H-5.33; N-22.41. Calc. %: C-57.95; H-5.27; N-22.53.

(d) N-Isopropyl-N'-[4-(2-methoxy-imidazol-4-yl)phenyl]-formamidine

Maleate salt (methanol). M.p. 236° C. (dec.).

Analysis: $C_{22}H_{26}N_4O_9$ Found %: C-54.02; H-5.46; N-11.53. Calc. %: C-53.87; H-5.34; N-11.42.

The compounds of the present invention, that is, those embraced by formula I above and their non-toxic, pharmacologically acceptable acid addition salts, have useful pharmacodynamic properties. More particularly, they exhibit $H_2$-receptor blocking activity in warm-blooded animals and thus inhibit gastric acid secretion, wherefore they are useful as anti-ulcerogenics.

The antagonistic effect of the compounds of the present invention of histamine $H_2$-receptors can be demonstrated either in vitro or in vivo by their inhibition of the $H_2$-dependent biological effects, which include the histamine-evoked positive chronotropic effect and the histamine-induced gastric secretion of acid, respectively.

The inhibition of the positive chronotropic effect was investigated in isolated guinea pig atria suspended in an organ bath (50 ml) containing oxygenated ($O_2$: 95%—$CO_2$: 5%) Krebs-Henseleit solution (pH 7.4) maintained at 32° C. The myocardial preparation, loaded with 1 g isometric tension, was allowed to stabilize for 60 minutes, and myocardial contractions were recorded through an isometric lever connected to a strain-gauge coupler, and the instantaneous rate was monitored with a cardiotachometer and a heat-writing pen recorder. After two control responses to histamine ($10^{-6}$ g.ml$^{-1}$) the test compounds were added to the bath at the desired final concentration and left for 30 minutes before the atria were again challenged with histamine. The chronotropic response obtained in the presence of the antagonist was then compared to the control response to histamine, and the percent reduction of the histamine $H_2$-evoked response was calculated. The average effective concentration ($EC_{50}$) of the $H_2$-antagonists was also calculated by standard procedure according to Dr. Waud, Analysis of dose-response curves, in "Methods in Pharmacology" vol. 3, Smooth muscle, Ed. Daniel E. E. Paton, M., Plenum Press. New York (1975); Ash and Schild, Br. J. Pharmacol. Chemother. 27, 427–439, 1966. The following table shows the obtained results:

TABLE I

| In vitro inhibitory activity in histamine-induced tachycardia (guinea pig atria). | |
|---|---|
| Compound of Example No. | $EC_{50}$ $10^{-7}$ M |
| 16 (a) | 1.5 |
| 16 (b) | 1.8 |
| 16 (c) | 1.2 |
| 17 | 4.0 |
| 16 (aa) | 1.94 |
| Cimetidine | 34.0 |

The ability of the test compounds to inhibit histamine-induced gastric secretion of acid was investigated after intravenous or intraduodenal administration in stomach perfused rats, according to Gosh and Schild [Br. J. Pharmacol. Chemother. 13, 54 (1958)]. The preparation of the animals in general anesthesia (urethane 1 g.kg$^{-1}$ i.p.) and constant temperature was achieved by inserting and tying in place polyethyl tubes (PE 50) in the esophagus and in the pyloric-antral region. After the stomach was washed to remove residuals of food, continuous perfusion of the stomach was started with saline, 0.5 ml.min$^{-1}$ (37° C.), primed by a Jobling peristaltic pump. After 30 minutes of perfusion adaptation, samples of the stomach perfusate were collected at 30 min. intervals and titrated for acid content, expressed as μEq of 1N NaOH. As control acid output became constant, intravenous perfusion of histamine (1 mg.kg$^{-1}$hr$^{-1}$) was started and maintained throughout the experimental period. After the acid secretion had reached the steadily higher level, increasing doses of the test compound were injected intravenously in order to obtain dose-response functions. The ED$_{50}$ was then calculated by standard procedure.

The results are reported in the following table:

TABLE II

In vivo antisecretory activity in histamine-induced gastric secretion (stomach perfused rat)

| Compound of Example No. | ED$_{50}$ mg.kg$^{-1}$ (i.v.)* |
|---|---|
| 16 (a) | 0.032 |
| 16 (b) | 0.067 |
| 16 (c) | 0.025 |
| 17 | 0.080 |
| 16 (aa) | 0.065 |
| Cimetidine | 0.560 |

*The values of activity are expressed taking the compound as a base.

Thus, by virtue of their superior activity as anti-secretory-antiulcer agents, the following compounds of the formula I are preferred for use in the treatment of disorders of the gastro-intestinal tract pursuant to the present invention:

N-Ethyl-N'-[4-(2-methyl-imidazol-4-yl)phenyl]-formamidine,

N-Isopropyl-N'-[4-(2-methyl-imidazol-4-yl)phenyl]-formamidine,

N-Allyl-N'-[4-(2-methyl-imidazol-4-yl)phenyl]-formamidine,

N-tert.Butyl-N'-[4-(2-methyl-imidazol-4-yl)phenyl]-formamidine, and

N-isopropyl-N'-[4-(2-hydroxy-imidazol-4-yl)phenyl]-formamidine.

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups and the like. An effective amount of the compounds according to the present invention is from 0.14 to 7.14 mgm/kg body weight, preferably 0.28 to 2.14 mgm/kg body weight.

The following examples illustrate a few pharmaceutical compositions comprising a compound of the present invention as an active ingredient and represent the best modes contemplated of using the invention. The parts are parts by weight unless otherwise specified.

EXAMPLE 19

Tablets

The tablet composition is compounded from the following ingredients:

| | |
|---|---|
| N—Ethyl-N'—[4-(2-methyl-imidazol-4-yl)phenyl]formamidine | 50 parts |
| Lactose | 217 parts |
| Corn starch | 30 parts |
| Magnesium stearate | 3 parts |
| Total | 300 parts |

Preparation:

The active ingredient, lactose and corn starch are mixed and homogeneously moistened with water. After screening of the moist mass and drying in a tray driver, the mixture is again passed through a screen and the magnesium stearate is added. Then, the mixture is compressed into 300 mg-tablets. Each tablet contains 50 mg of active ingredient.

EXAMPLE 20

Capsules

The capsule filler composition is compounded from the following ingredients:

| | |
|---|---|
| N—Isopropyl-N'—[4-(2-methyl-imidazol-4-yl)phenyl]formamidine | 50 parts |
| Corn starch | 170 parts |
| Magnesium stearate | 2 parts |
| Total | 222 parts |

Preparation:

The ingredients are combined, the mixture is passed through a screen, and the composition is homogenized in a suitable device. 222 mg-portions of the composition are filled into gelatin capsules of suitable size. Each capsule contains 50 mg of the active ingredient.

EXAMPLE 21

Hypodermic solution

The solution is compounded from the following ingredients:

| | |
|---|---|
| N—Allyl-N'—[4-(2-methyl-imidazol-4-yl)phenyl]formamidine | 50 parts |
| Water for injection q.s.ad | 5000 parts by vol. |

Preparation:

The active ingredient is dissolved in the appropriate amount of water and the resulting solution is filled into 5 cc-ampules under sterile conditions. Each ampule contains 50 mg of the active ingredient.

Any one of the other compounds embraced by formula I or a non-toxic, pharmacologically acceptable acid addition salt thereof may be substituted for the particular active ingredient in Examples 19 through 21. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

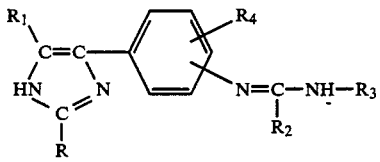

wherein
- R is straight or branched lower alkyl, hydroxyl, alkoxy of 1 to 3 carbon atoms, mercapto, (alkyl of 1 to 3 carbon atoms)thio, halogen, (alkyl of 1 to 3 carbon atoms)sulfinyl, (alkyl of 1 to 3 carbon atoms)sulfonyl, sulfamoyl, amino, (alkyl of 1 to 3 carbon atoms)amino, di(alkyl of 1 to 3 carbon atoms)amino, lower alkanoylamino or phenyl;
- $R_1$ and $R_2$ are each independently hydrogen or lower alkyl;
- $R_3$ is straight or branched lower alkyl, hydroxy(alkyl of 1 to 6 carbon atoms), (alkoxy of 1 to 6 carbon atoms)-(alkyl of 1 to 6 carbon atoms), (alkyl of 1 to 6 carbon atoms)thio(alkyl of 1 to 6 carbons atoms), cyano(alkyl of 1 to 6 carbon atoms), lower alkenyl, lower alkynyl, cyano, phenyl, chlorophenyl, benzyl, cyclo lower alkyl, cyclo lower alkyl(alkyl of 1 to 2 carbon atoms) or an aromatic 5- to 6-membered heterocyclic ring containing one heteroatom; and
- $R_4$ is hydrogen, alkyl of 1 to 3 carbon atoms, alkoxy of 1 to 3 carbon atoms, halogen, cyano or carbamoyl;

a tautomer thereof, or a non-toxic, pharmacologically acceptable acid addition salt thereof.

2. A compound of claim 1, which is N-ethyl-N'-[4-(2-methyl-imidazol-4-yl)phenyl]formamidine or a non-toxic, pharmacologically acceptable acid addition salt thereof.

3. A compound of claim 1, which is N-isopropyl-N'-[4-(2-methyl-imidazol-4-yl)phenyl]formamidine or a non-toxic, pharmacologically acceptable acid addition salt thereof.

4. A compound of claim 1, which is N-allyl-N'-[4-(2-methyl-imidazol-4-yl)phenyl]formamidine or a non-toxic, pharmacologically acceptable acid addition salt thereof.

5. A compound of claim 1, which is N-tert.butyl-N'-[4-(2-methyl-imidazol-4-yl)phenyl]formamidine or a non-toxic, pharmacologically acceptable acid addition salt thereof.

6. A compound of claim 1, which is N-isopropyl-N'-[4-(2-hydroxy-imidazol-4-yl)phenyl]formamidine or a non-toxic, pharmacologically acceptable acid addition salt thereof.

7. A compound of claim 1, where said acid addition salt is a hydrochloride, sulfate, maleate or fumarate.

8. An antiulcerogenic pharmaceutical composition consisting essentially of an inert pharmaceutical carrier and an effective antiulcerogenic amount of a compound of claim 1.

9. The method of treating gastrointestinal ulcers in a warm-blooded animal in need thereof, which comprises perorally or parenterally administering to said animal an effective antiulcerogenic amount of a compound of claim 1.

10. A compound of the formula

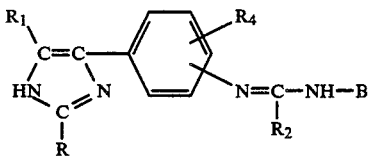

wherein R, $R_1$, $R_2$ and $R_4$ have the meanings defined in claim 1, and B is cyano, acetyl, carbethoxy or carbamoyl.

* * * * *